(12) United States Patent
Yamashita

(10) Patent No.: US 7,577,288 B2
(45) Date of Patent: Aug. 18, 2009

(54) SAMPLE INSPECTION APPARATUS, IMAGE ALIGNMENT METHOD, AND PROGRAM-RECORDED READABLE RECORDING MEDIUM

(75) Inventor: Kyoji Yamashita, Kanagawa (JP)

(73) Assignee: Advanced Mask Inspection Technology Inc., Yokohama-shi (JP)

( * ) Notice: Subject to any disclaimer, the term of this patent is extended or adjusted under 35 U.S.C. 154(b) by 689 days.

(21) Appl. No.: 11/287,419

(22) Filed: Nov. 28, 2005

(65) Prior Publication Data

US 2007/0053582 A1 Mar. 8, 2007

(30) Foreign Application Priority Data

Sep. 6, 2005 (JP) ............................. 2005-257606

(51) Int. Cl.
*G06K 9/00* (2006.01)
(52) U.S. Cl. ...................... 382/145; 382/144; 382/149
(58) Field of Classification Search ................. 382/144
See application file for complete search history.

(56) References Cited

U.S. PATENT DOCUMENTS

| | | | | |
|---|---|---|---|---|
| 4,805,123 A | * | 2/1989 | Specht et al. ............... | 382/144 |
| 5,153,444 A | * | 10/1992 | Maeda et al. ........... | 250/559.05 |
| 5,404,410 A | * | 4/1995 | Tojo et al. .................. | 382/144 |
| 5,563,702 A | | 10/1996 | Emery et al. | |
| 5,659,172 A | * | 8/1997 | Wagner et al. ............... | 250/307 |
| 5,949,901 A | * | 9/1999 | Nichani et al. .............. | 382/149 |
| 5,960,106 A | * | 9/1999 | Tsuchiya et al. ............ | 382/144 |
| 5,995,219 A | * | 11/1999 | Tabata ..................... | 356/237.5 |
| 6,041,140 A | * | 3/2000 | Binns et al. ................. | 382/209 |
| 6,107,637 A | * | 8/2000 | Watanabe et al. ........ | 250/559.3 |
| 6,396,943 B2 | | 5/2002 | Yamashita | |
| 6,628,845 B1 | * | 9/2003 | Stone et al. ................. | 382/294 |

(Continued)

FOREIGN PATENT DOCUMENTS

JP 63-88682 4/1988

(Continued)

OTHER PUBLICATIONS

U.S. Appl. No. 11/678,748, filed Feb. 26, 2007, Yamashita.

(Continued)

*Primary Examiner*—Brian P Werner
*Assistant Examiner*—Jayesh Patel
(74) *Attorney, Agent, or Firm*—Oblon, Spivak, McClelland, Maier & Neustadt, P.C.

(57) ABSTRACT

A sample inspection apparatus according to an aspect of the present invention includes a first SSD calculating unit which calculates the displacement amount from a preliminary alignment position of an optical image and a reference image to a position where the SSD of a pixel value of the optical image and a pixel value of the reference image is minimized, and a least-square method calculating unit which calculates the displacement amount by a least-square method from the preliminary alignment position of the optical image and the reference image, wherein the alignment position of the optical image and the reference image is corrected to a position where the smaller SSD of the minimum SSD obtained as the result of the calculation by the first SSD calculating unit and the SSD obtained as the result of the calculation by the determined by the least-square method calculating unit is obtained.

9 Claims, 11 Drawing Sheets

U.S. PATENT DOCUMENTS

| | | | |
|---|---|---|---|
| 6,947,587 B1 * | 9/2005 | Maeda et al. | 382/149 |
| 7,032,208 B2 * | 4/2006 | Yamashita | 716/19 |
| 2004/0114218 A1 * | 6/2004 | Karlsson et al. | 359/368 |

FOREIGN PATENT DOCUMENTS

| | | |
|---|---|---|
| JP | 3-278057 | 12/1991 |
| JP | 5-281154 | 10/1993 |
| JP | 6-307826 | 11/1994 |
| JP | 8-64511 | 3/1996 |
| JP | 8-76359 | 3/1996 |
| JP | 8-77357 | 3/1996 |
| JP | 8-304997 | 11/1996 |
| JP | 10-96613 | 4/1998 |
| JP | 10-318950 | 12/1998 |
| JP | 11-132959 | 5/1999 |
| JP | 11-153550 | 6/1999 |
| JP | 2000-348177 | 12/2000 |
| JP | 2001-141677 | 5/2001 |
| JP | 2002-14062 | 1/2002 |
| JP | 2004-317427 | 11/2004 |

OTHER PUBLICATIONS

U.S. Appl. No. 11/692,352, filed Mar. 28, 2007, Yamashita.

M. Takagi, et al. "Handbook on Image Analysis"; University of Tokyo Press; Jan. 17, 1991; pp. 442-443 (with Partial English Translation).

\* cited by examiner $$\begin{cases} S(x,y) = (1-\varepsilon) \cdot U(x-x_0, y-y_0) \cdots & (1) \\ \varepsilon \cdot U + x_0 \cdot \dfrac{\partial U}{\partial x} + y_0 \dfrac{\partial U}{\partial y} = U - S \cdots & (2) \end{cases}$$

FIG.6

$$\begin{pmatrix} \sum U^2 & \sum U \dfrac{\partial U}{\partial x} & \sum U \dfrac{\partial U}{\partial y} \\ \sum U \dfrac{\partial U}{\partial x} & \sum (\dfrac{\partial U}{\partial x})^2 & \sum \dfrac{\partial U}{\partial x} \dfrac{\partial U}{\partial y} \\ \sum U \dfrac{\partial U}{\partial y} & \sum \dfrac{\partial U}{\partial x} \dfrac{\partial U}{\partial y} & \sum (\dfrac{\partial U}{\partial y})^2 \end{pmatrix} \begin{pmatrix} \varepsilon \\ x_0 \\ y_0 \end{pmatrix} = \begin{pmatrix} \sum (U-S)U \\ \sum (U-S)\dfrac{\partial U}{\partial x} \\ \sum (U-S)\dfrac{\partial U}{\partial y} \end{pmatrix}$$

FIG.7

$$10 \longrightarrow \sum\left(\frac{\partial U}{\partial x}\right)^2 \gg \sum\left(\frac{\partial U}{\partial y}\right)^2$$

$$12 \longrightarrow \begin{pmatrix} \sum U^2 & \sum U \frac{\partial U}{\partial x} \\ \sum U \frac{\partial U}{\partial x} & \sum\left(\frac{\partial U}{\partial x}\right)^2 \end{pmatrix} \begin{pmatrix} \varepsilon \\ x_0 \end{pmatrix} = \begin{pmatrix} \sum (U-S)U \\ \sum (U-S)\frac{\partial U}{\partial x} \end{pmatrix}$$

FIG.10

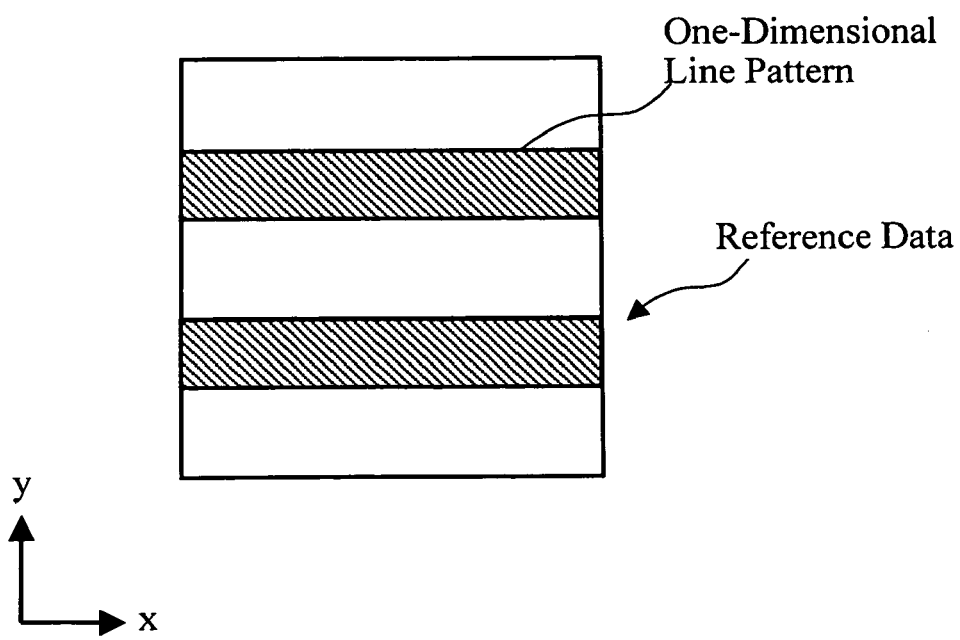

FIG.11

$$\begin{cases} U_{(0)} = (1-x) \cdot (1-y) \cdot U \\ U_{(1)} = x \cdot (1-y) \cdot U \\ U_{(2)} = x \cdot y \cdot U \\ U_{(3)} = (1-x) \cdot y \cdot U \end{cases}$$

$$\begin{pmatrix} \sum U_{(0)}^2 & \cdots & \sum U_{(0)}U_{(3)} & \sum U_{(0)}\frac{\partial U_{(0)}}{\partial x} & \cdots & \sum U_{(0)}\frac{\partial U_{(3)}}{\partial x} & \sum U_{(0)}\frac{\partial U_{(0)}}{\partial y} & \cdots & \sum U_{(0)}\frac{\partial U_{(3)}}{\partial y} \\ \vdots & \ddots & \vdots & \vdots & \ddots & \vdots & \vdots & \ddots & \vdots \\ \sum U_{(3)}U_{(0)} & \cdots & \sum U_{(3)}^2 & \sum U_{(3)}\frac{\partial U_{(0)}}{\partial x} & \cdots & \sum U_{(3)}\frac{\partial U_{(3)}}{\partial x} & \sum U_{(3)}\frac{\partial U_{(0)}}{\partial y} & \cdots & \sum U_{(3)}\frac{\partial U_{(3)}}{\partial y} \\ \sum \frac{\partial U_{(0)}}{\partial x}U_{(0)} & \cdots & \sum \frac{\partial U_{(0)}}{\partial x}U_{(3)} & \sum (\frac{\partial U_{(0)}}{\partial x})^2 & \cdots & \sum \frac{\partial U_{(0)}}{\partial x}\frac{\partial U_{(3)}}{\partial x} & \sum \frac{\partial U_{(0)}}{\partial x}\frac{\partial U_{(0)}}{\partial y} & \cdots & \sum \frac{\partial U_{(0)}}{\partial x}\frac{\partial U_{(3)}}{\partial y} \\ \vdots & \ddots & \vdots & \vdots & \ddots & \vdots & \vdots & \ddots & \vdots \\ \sum \frac{\partial U_{(3)}}{\partial x}U_{(0)} & \cdots & \sum \frac{\partial U_{(3)}}{\partial x}U_{(3)} & \sum \frac{\partial U_{(3)}}{\partial x}\frac{\partial U_{(0)}}{\partial x} & \cdots & \sum (\frac{\partial U_{(3)}}{\partial x})^2 & \sum \frac{\partial U_{(3)}}{\partial x}\frac{\partial U_{(0)}}{\partial y} & \cdots & \sum \frac{\partial U_{(3)}}{\partial x}\frac{\partial U_{(3)}}{\partial y} \\ \sum \frac{\partial U_{(0)}}{\partial y}U_{(0)} & \cdots & \sum \frac{\partial U_{(0)}}{\partial y}U_{(3)} & \sum \frac{\partial U_{(0)}}{\partial y}\frac{\partial U_{(0)}}{\partial x} & \cdots & \sum \frac{\partial U_{(0)}}{\partial y}\frac{\partial U_{(3)}}{\partial x} & \sum (\frac{\partial U_{(0)}}{\partial y})^2 & \cdots & \sum \frac{\partial U_{(0)}}{\partial y}\frac{\partial U_{(3)}}{\partial y} \\ \vdots & \ddots & \vdots & \vdots & \ddots & \vdots & \vdots & \ddots & \vdots \\ \sum \frac{\partial U_{(3)}}{\partial y}U_{(0)} & \cdots & \sum \frac{\partial U_{(3)}}{\partial y}U_{(3)} & \sum \frac{\partial U_{(3)}}{\partial y}\frac{\partial U_{(0)}}{\partial x} & \cdots & \sum \frac{\partial U_{(3)}}{\partial y}\frac{\partial U_{(3)}}{\partial x} & \sum \frac{\partial U_{(3)}}{\partial y}\frac{\partial U_{(0)}}{\partial y} & \cdots & \sum (\frac{\partial U_{(3)}}{\partial y})^2 \end{pmatrix} \begin{pmatrix} \varepsilon_{(0)} \\ \vdots \\ \varepsilon_{(3)} \\ x_{0(0)} \\ \vdots \\ x_{0(3)} \\ y_{0(0)} \\ \vdots \\ y_{0(3)} \end{pmatrix} = \begin{pmatrix} \sum (U_{(0)}-S_{(0)})U_{(0)} \\ \vdots \\ \sum (U_{(3)}-S_{(3)})U_{(3)} \\ \sum (U_{(0)}-S_{(0)})\frac{\partial U_{(0)}}{\partial x} \\ \vdots \\ \sum (U_{(3)}-S_{(3)})\frac{\partial U_{(3)}}{\partial x} \\ \sum (U_{(0)}-S_{(0)})\frac{\partial U_{(0)}}{\partial y} \\ \vdots \\ \sum (U_{(3)}-S_{(3)})\frac{\partial U_{(3)}}{\partial y} \end{pmatrix}$$

FIG.16

SAMPLE INSPECTION APPARATUS, IMAGE ALIGNMENT METHOD, AND PROGRAM-RECORDED READABLE RECORDING MEDIUM

CROSS-REFERENCE TO RELATED APPLICATION

This application is based upon and claims the benefit of priority from prior Japanese Patent Application No. 2005-257606 filed on Sep. 6, 2005 in Japan, the entire contents of which are incorporated herein by reference.

BACKGROUND OF THE INVENTION

1. Field of the Invention

The present invention relates to a sample inspection apparatus, an image alignment method, or a program which causes a computer to execute the method, such as a pattern inspection technique which inspects a pattern defect of an object serving as a sample used in manufacturing a semiconductor, and an apparatus which inspects a defect of a ultra-fine pattern of a photomask, a wafer, or a liquid crystal substrate used in manufacturing a semiconductor device or a liquid crystal display (LCD).

2. Related Art

In recent years, with highly integrated and a large volume of large-scale integrated circuits (LSI), a circuit line width that cutting-edge semiconductor devices require shrinks greatly. These semiconductor devices are manufactured such that a pattern is exposed and transferred onto a wafer by a reduced-magnification projection exposure apparatus (a wafer stepper) while using a master pattern of a circuit pattern formed thereupon (The master pattern is also called a mask or a reticle. The master pattern will be generally called as a mask hereinafter.) to form a circuit. Therefore, in manufacturing a mask to transfer fine circuit patterns onto a wafer, a pattern writing device which can draw a fine circuit pattern is deployed. A pattern writing device may directly draw a pattern circuit. Alternatively, in addition to an electronic beam writing (apparatus), a laser beam writing apparatus (which draws a pattern by using a laser beam) is deployed alternatively.

An improvement in yield is crucial in manufacturing an LSI which requires a lot of manufacturing cost. However, as represented by a one-gigabit DRAM (Random Access Memory), the orecision of a pattern constituting an LSI has been changing from a sub-micron precision realm to a nano precision realm. One of crucial factors which decrease yield, is pattern defects of a mask that is used when an ultrafine pattern is exposed and transferred onto a semiconductor wafer by a photolithography technique is well-known. In recent years, with a miniaturization of an LSI pattern formed onto a semiconductor wafer, a size which has to be detected as a pattern defect has also become considerably small. For this reason, a pattern inspection apparatus which inspects a defect of a transfer mask used in manufacturing an LSI must be increased in precision.

On the other hand, with development of multimedia, a liquid crystal display (LCD) has a liquid crystal substrate size of 500 mm×600 mm or larger, and micropatterning of a thin film transistor (TFT) or the like formed on a liquid crystal substrate advances. Therefore, it is required that a considerably small pattern defect be inspected in a large area. For this reason, development of a sample inspection apparatus which efficiently inspects a defect of a pattern of a large-area LCD and a photomask used in manufacturing the large-area LCD in a reasonable period of time is urgently required.

In this case, in a conventional pattern inspection apparatus, it is well-known that an optical image obtained by scanning up an image of a pattern formed on a sample such as a lithography mask or the like at a predetermined magnification by using a magnifying optical system is compared with design data or an optical image obtained by scanning image of the same pattern on the sample to perform inspection (for example, see Japanese Patent Application, Publication No.HEI08-76359).

For example, as pattern inspection methods, there are well-known "die to die inspection" which compares optical image data obtained by scanning images of the same patterns at different places on the same mask, and "die to database inspection" which inputs data (design pattern data) obtained by converting CAD data into appropriate format to be inputted by a drawing apparatus in drawing a pattern on a mask into an inspection apparatus, generates design image data (reference image) on the basis thereof, and compares the design image data with an optical image serving as measurement data obtained by scanning the image of the pattern. In the inspection methods in the inspection apparatus, a sample is placed on a stage, and a flux of light scans the sample as a result of the movement of the stage to perform inspection. The flux of light is irradiated on the sample from a light source and an illumination optical system. Light transmitted through the sample or reflected by the sample is focused on a CCD sensor through an optical system. The image scanned using the CCD sensor is transmitted to a comparing circuit as measurement data. In the comparing circuit, after alignment of the images, the measurement data is compared with reference data based on sofisticated algorithm. When the measurement data is different from the reference data, it locates a pattern defect as a defect.

Herein, the reference image and the optical image are compared per a predetermined size of area, and for this comparison, highly precise alignment between the reference image and the optical image is required. Herein, a technique for calculating the displacement amount between a reference image and an optical image by use of a least-square method is disclosed in a reference (for example, refer to Japanese Patent Application, Publication No.HEI11-153550). Further, an interpolation method for interpolating image data to be obtained by use of neiboring 4-point or 16-point image data is described in a reference (for example, refer to Image Analysis Handbook, pages 442 to 443, University of Tokyo Press, first edition issued on Jan. 17, 1991).

However, with a miniaturization of a pattern, there is a demand for a further precision of alignment required for detecting ultrafine defects. The point herein is to correct only systematic error factors such as a stage placement error, a speed error or a magnification error, but not to correct inconsistent portions that occur locally and randomly such as defects.

As described above, highly precise alignment between the reference image and the optical image is required for the comparison. However, with a miniaturization of a pattern, it has become difficult to detect the relative displacement between the reference image and the optical image in high precision.

BRIEF SUMMARY OF THE INVENTION

An aspect of the present invention has as its object to provide a method and apparatus which overcome the above problems and perform a highly precise alignment between a reference image and an optical image.

A sample inspection apparatus according to an aspect of the present invention comprises:

an optical image scanning unit which scans an optical image of a sample to be inspected;

a reference image generating unit which generates a reference image to be compared with the optical image on the basis of design data of the sample to be inspected;

a first SSD (Sum of the Squared Difference) calculating unit which calculates the displacement amount from a preliminary alignment position of the optical image and the reference image to a position where the SSD (Sum of the Squared Difference) of a pixel value of the optical image and a pixel value of the reference image are minimized;

a least-square method calculating unit which calculates the displacement amount by least-square method from the preliminary alignment position of the optical image and the reference image;

a second SSD calculating unit which calculates the SSD of the pixel value of the optical image and the pixel value of the reference image at a position displaced by the displacement amount calculated by the least-square method calculating unit from the preliminary alignment position of the optical image and the reference image;

a determining unit which determines which of the minimum SSD obtained as the result of the calculation by the first SSD calculating unit and the SSD obtained as the result of the calculation by the second SSD calculating unit is smaller;

a position correcting unit which corrects the alignment position of the optical image and the reference image to a position where the smaller SSD determined by the determining unit is obtained; and a comparing unit which compares the optical image and the reference image whose alignment position has been corrected.

An image alignment method for aligning an optical image and a reference image for use in a comparison inspection of a sample to be inspected in such an apparatus, comprises:

calculating the displacement amount from a preliminary alignment position of the optical image and the reference image to a position of a first SSD where is a minimum SSD between a pixel value of the optical image and a pixel value of the reference image;

calculating the displacement amount by a least-square method from the preliminary alignment position of the optical image and the reference image;

calculating a second SSD of the pixel value of the optical image and the pixel value of the reference image at a position displaced by the displacement amount calculated by the least-square method from the preliminary alignment position of the optical image and the reference image;

determining which of the first SSD and the second SSD is smaller; and correcting the alignment position of the optical image and the reference image to a position where the smaller SSD determined is obtained.

According to another aspect of the present invention, there is provided a readable recording medium having recorded therein a program for causing a computer to execute:

a storing process for storing an optical image and a reference image used for a comparison inspection of a sample to be inspected in a storage device;

a first SSD calculating process for calculating the displacement amount from a preliminary alignment position of the optical image and the reference image to a position where the SSD between a pixel value of the optical image and a pixel value of the reference image becomes minimum by reading the optical image and the reference image from the storage device;

a least-square method calculating process for calculating the displacement amount by a least-square method from the preliminary alignment position of the optical image and the reference image by reading the optical image and the reference image from the storage device;

a second SSD calculating process for calculating the SSD of the pixel value of the optical image and the pixel value of the reference image at a position displaced by the displacement amount calculated by the least-square method calculating process from the preliminary alignment position of the optical image and the reference image;

a determining process for determining which of the minimum SSD obtained as the result of the calculation by the first SSD calculating process and the SSD obtained as the result of the calculation by the second SSD calculating process is smaller; and a position correcting process for correcting the alignment position of the optical image and the reference image to a position where the smaller SSD determined by the determining process is obtained.

BRIEF DESCRIPTION OF THE DRAWINGS

FIG. 6 shows a model equation for displacement amount calculation based on a least-square method;

FIG. 7 shows a correlation matrix equation based on the least-square method;

FIG. 10 shows a correlation matrix equation in the case where calculation of the $y_0$ parameter becomes unstable;

FIG. 11 is a diagram showing still another example of a one-dimensional pattern (lines and spaces);

FIG. 16 shows a correlation matrix equation in a third embodiment; and

DETAILED DESCRIPTION OF THE INVENTION

First Embodiment

Figure 1:
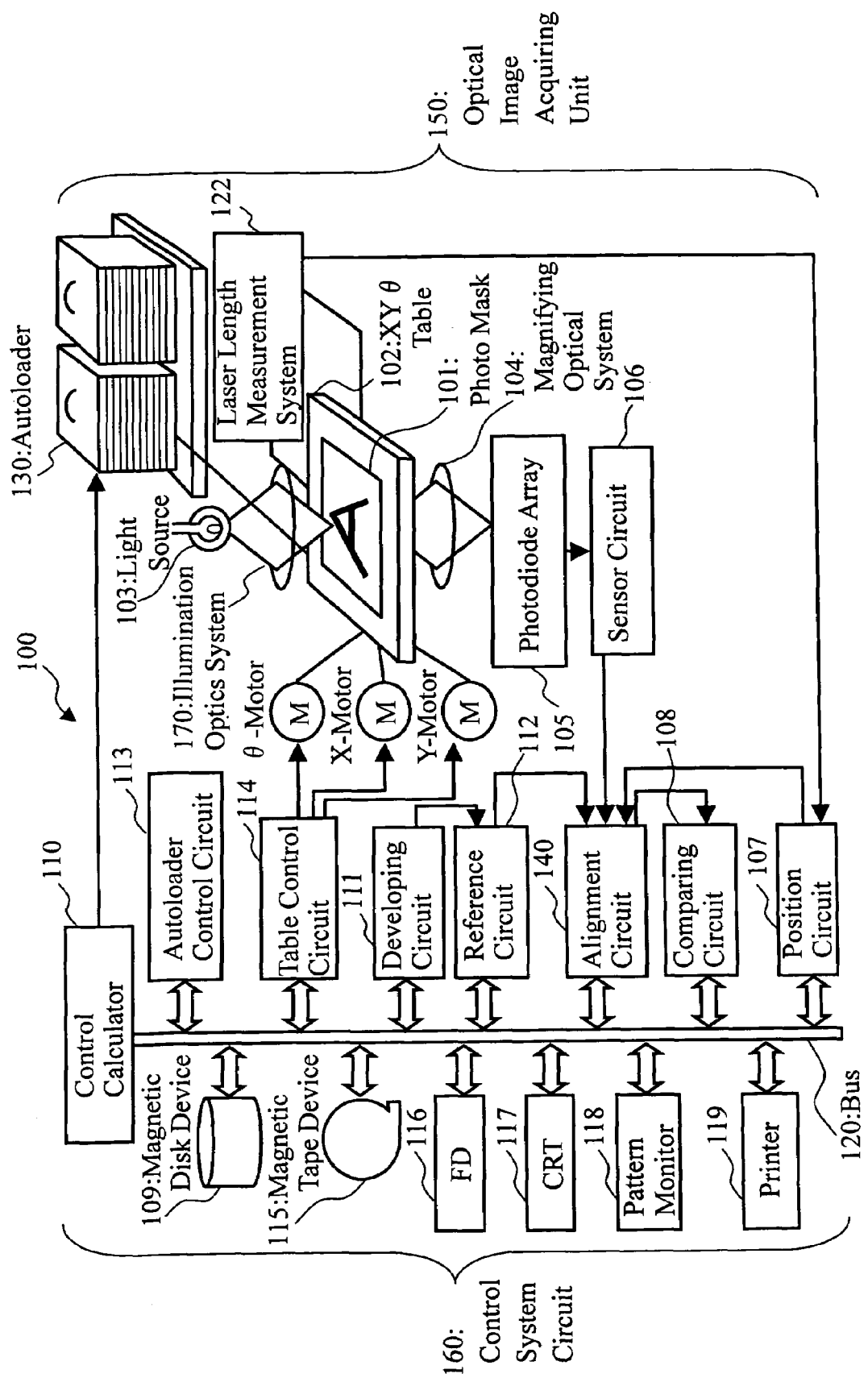
FIG. 1 is a schematic diagram showing the configuration of a sample inspection apparatus according to a first embodiment.

FIG. 1 is a conceptual diagram showing the configuration of a sample inspection apparatus according to a first embodiment.

In FIG. 1, a sample inspection apparatus 100 which inspects a defect of a substrate such as a mask or a wafer serving as a sample includes an optical image scanning unit 150 and a control system circuit 160. The optical image scanning unit 150 includes an XYθ table 102, a light source 103, a magnifying optical system 104, a photodiode array 105, a sensor circuit 106, a laser length measurement system 122, an autoloader 130, and an illumination optical system 170. In the control system circuit 160, a control calculator 110 serving as a computer is connected, through data bus 120 serving as a data transmission path, to a position circuit 107, a comparing circuit 108, a developing circuit 111, a reference circuit 112, an alignment circuit 140, an autoloader control circuit 113, a table control circuit 114, a magnetic disk device 109, a magnetic tape device 115, a flexible disk device (FD) 116, a CRT 117, a pattern monitor 118, and a printer 119. The XYθ table 102 is driven by an X-axis motor, a Y-axis motor, and a θ-axis monitor. In FIG. 1, units except for constituent units necessary for explaining the first embodiment are omitted. The sample inspection apparatus 100 generally includes other necessary constituent elements as a matter of course.

Figure 2:
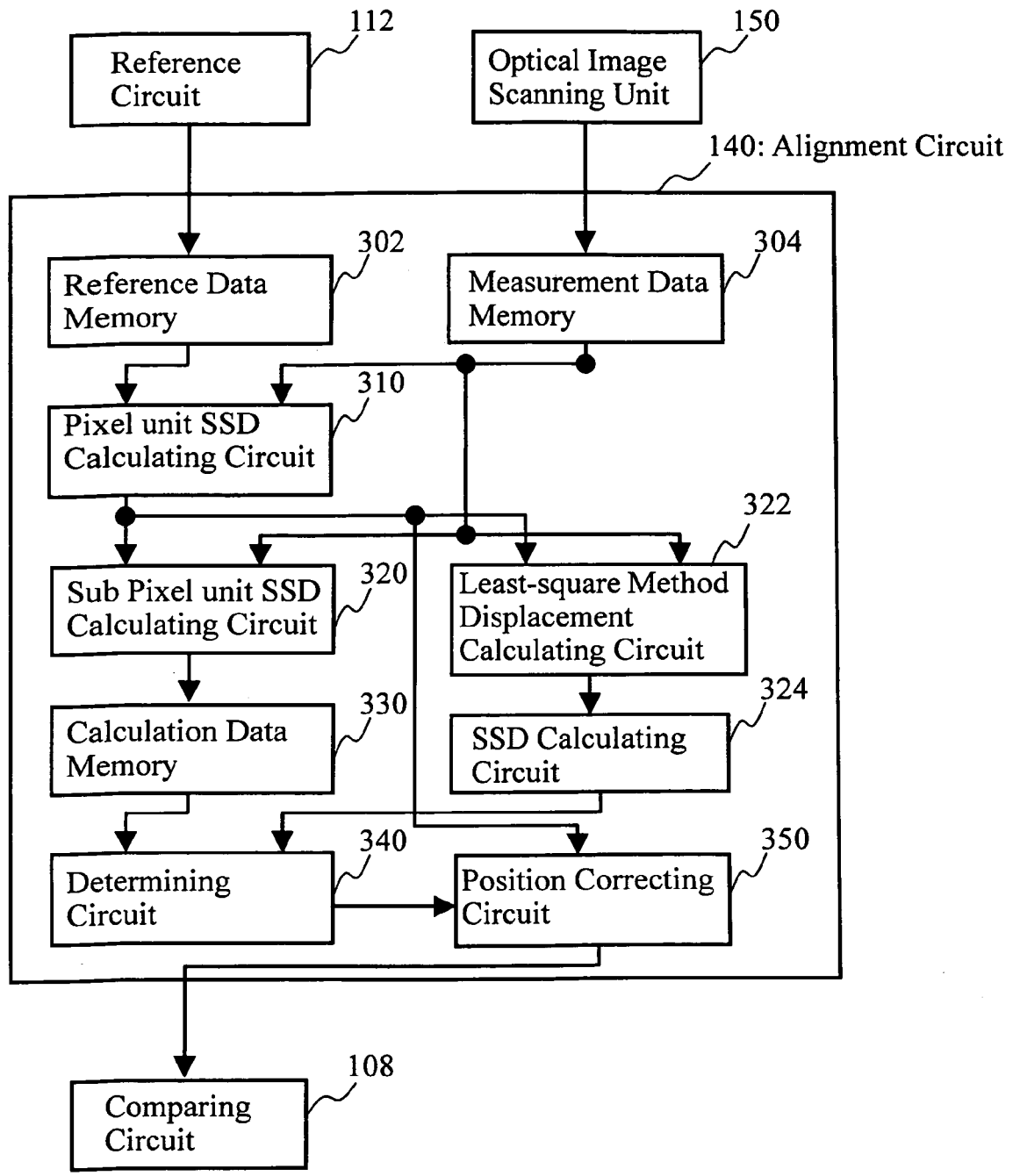
FIG. 2 is a block diagram showing the configuration of an alignment circuit.

FIG. 2 is a block diagram showing an example of the configuration of the alignment circuit.

In FIG. 2, the alignment circuit 140 includes a reference data memory 302, a measurement data memory, a pixel unit SSD (Sum of the Squared Difference) calculating circuit 310, a sub pixel unit SSD calculating circuit 320, a least-square method displacement calculating circuit 322, a calculation data memory 330, a SSD calculating circuit 324, a determining circuit 340, and a position correcting circuit 350. The alignment circuit 140 receives reference data from the reference circuit 120 and measurement data from the optical image scanning unit 150, performs the alignment of these items of data, and outputs the reference data and the measurement data to the comparing circuit 108.

Figure 3:
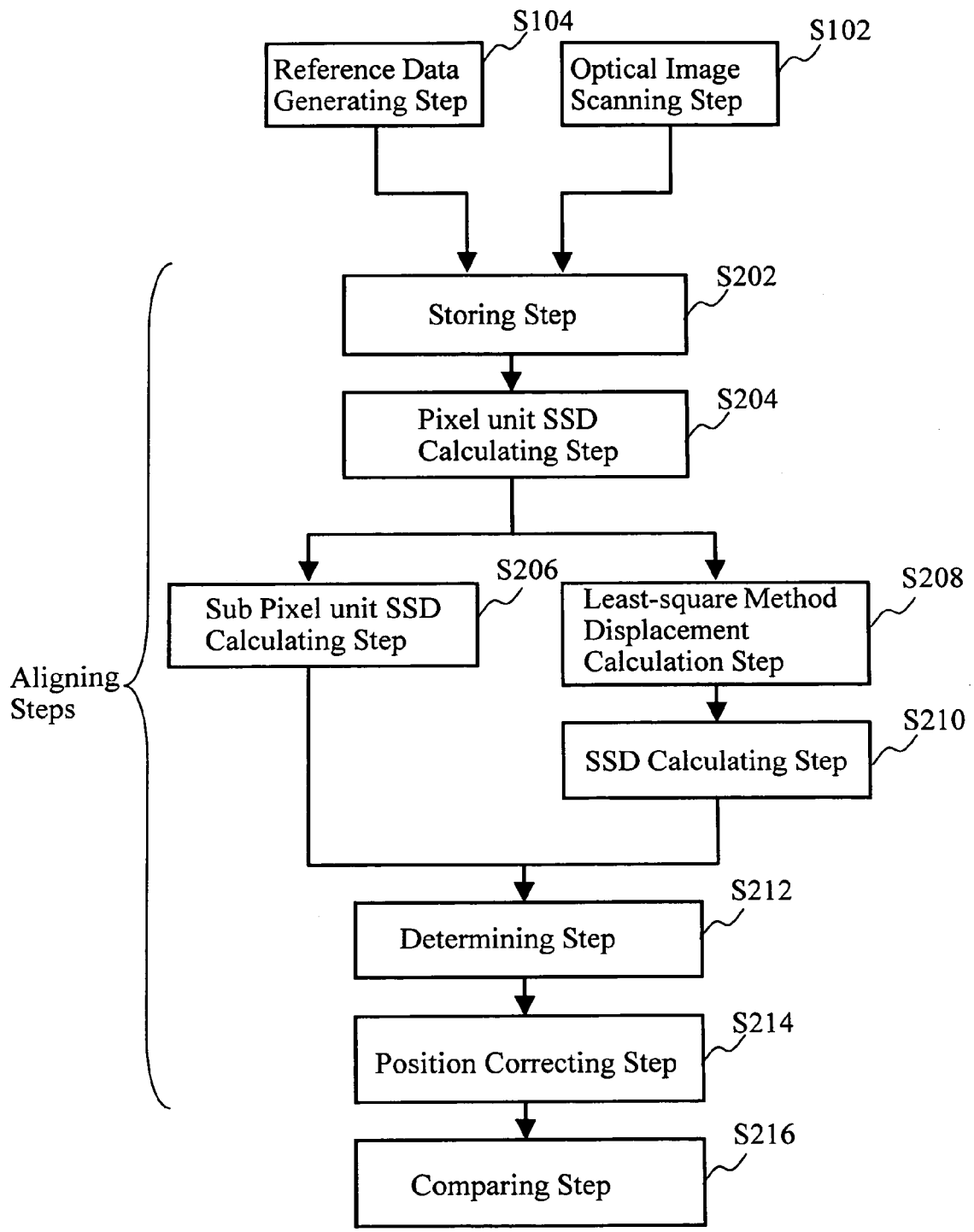
FIG. 3 is a flow chart showing main steps of a sample inspection method according to the first embodiment.

FIG. 3 is a flow chart showing main steps of a sample inspection method according to the first embodiment.

In FIG. 3, the sample inspection method executes a series of steps including an optical image scanning step (S102), a reference data generating step (S104), a alignment step, and a comparing step (S216). As the aligning step as one example of an image alignment method, a series of steps including a storing step (S202), a pixel unit SSD calculating step (S204), a sub pixel unit SSD calculating step (S206), a least-square method displacement calculating step (S208), a SSD calculating step (S210), a determining step (S212), and a position correcting step (S214) are executed.

In S (step) 102, as the optical image scanning step, the optical image scanning unit 150 scans an optical image of a photomask 101 serving as a sample on which an image expressed by image data included in design data are drawn based on the design data. More specifically, the optical image is scanned as follows.

The photomask 101 serving as a sample to be inspected is placed on the XYθ table 102 which is arranged such that the XYθ table 102 can be moved in a horizontal direction and a rotating direction by the X-, Y-, and θ-axis motors. On the pattern formed on the photomask 101, light is irradiated by the appropriate light source 103 arranged above the XYθ table 102. A flux of light irradiated from the light source 103 is irradiated on the photomask 101 serving as a sample through the illumination optical system 170. Below the photomask 101, the magnifying optical system 104, the photodiode array 105, and the sensor circuit 106 are arranged. The light transmitted through the photomask 101 serving as a sample such as an exposure mask is focused on the photodiode array 105 as an optical image through the magnifying optical system 104 and enters the photodiode array 105.

Figure 4:
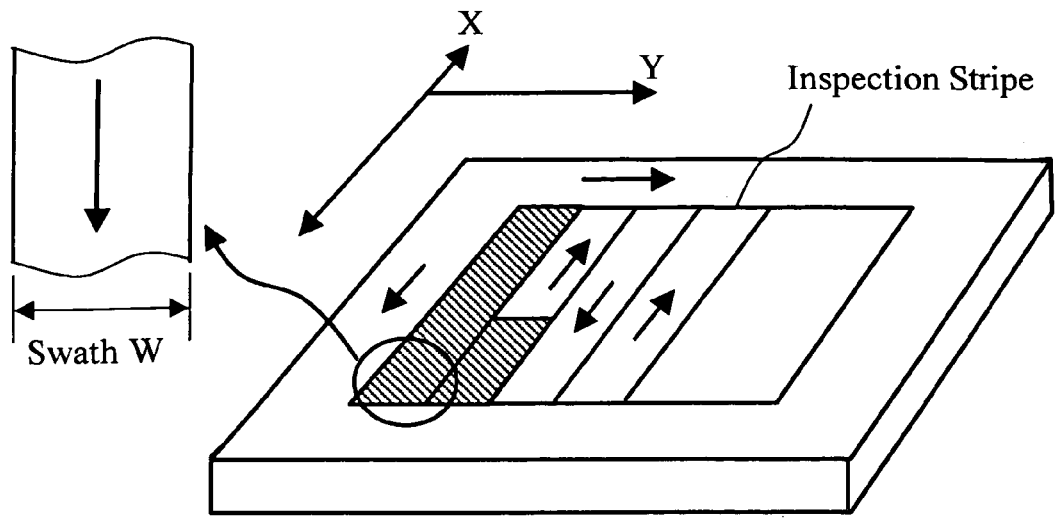
FIG. 4 is a diagram for explaining a procedure of scanning an optical image.

FIG. 4 is a diagram for explaining a procedure for scanning an optical image.

A region to be inspected is, as shown in FIG. 4, virtually divided into a plurality of strip-like inspection stripes each having a scan swath W in a Y direction, and the operation of the XYθ table 102 is controlled such that the divided inspection stripes are continuously scanned. While the XYθ table 102 moves in the X direction, an optical image is acquired. In the photodiode array 105, images each having the scan swath W as shown in FIG. 4 are continuously inputted. After an image on a first inspection stripe is scanned, images each having the scan swath W are continuously inputted while an image on a second inspection stripe is moved in the reverse direction at this time. When an image on a third inspection stripe is to be scanned, the image is scanned while the image is moved in the direction reverse to the direction for scanning the image on the second inspection stripe, i.e., the direction for scanning the image on the first inspection stripe. In this manner, the images are continuously acquired to make it possible to shorten wasteful processing time.

The image of the pattern focused on the photodiode array 105 is photo-electrically converted by the photodiode array 105. Furthermore, the electric image is A/D-converted (analog to digital-converted) by the sensor circuit 106. In the photodiode array 105, a sensor such as a TDI (Time Delay and Integration) sensor is arranged. The XYθ table 102 serving as a stage is continuously moved in the X-axis direction to cause the TDI sensor to scan the image of the pattern of the photomask 101 serving as a sample. An inspection optical system having a large magnification is constituted by the light source 103, the magnifying optical system 104, the photodiode array 105, and the sensor circuit 106.

The XYθ table 102 is driven by the table control circuit 114 under the control of the control calculator 110. The XYθ table 102 can be moved by a drive system such as three-axis (X-Y-θ) motors which drive the XYθ table 102 in the X direction, the Y direction, and the θ direction.

Measurement data (optical image) output from the sensor circuit 106 is transmitted to the alignment circuit 140 together with data output from the position circuit 107 and representing the position of the photomask 101 on the XYθ table 102. The measurement data is, for example, 8-bit unsigned data, and expresses gray levels of respective pixels.

Then, in step S102, as the reference data generating step, a developing circuit 111 and a reference circuit 112 serving as one example of a reference image generating unit generates reference data (reference image) for comparison with measurement data on the basis of design data of the photo mask 101 serving as a sample to be inspected.

Next, as the aligning step, alignment is performed for comparing the measurement data and the reference data.

In step S202, as the storing step, the reference data is read and stored in the reference data memory 302 by use of the control calculator 110. In the same manner, the measurement data is read and stored in the measurement data memory 304.

In step S204, as the pixel unit SSD calculating step, the pixel unit SSD calculating circuit 310 serving as one example of an SSD calculating unit performs displacement in units of pixels, and calculates the displacement amount to a position where the SSD between a pixel value of the measurement data and a pixel value of the reference data becomes minimum.

Figure 5:
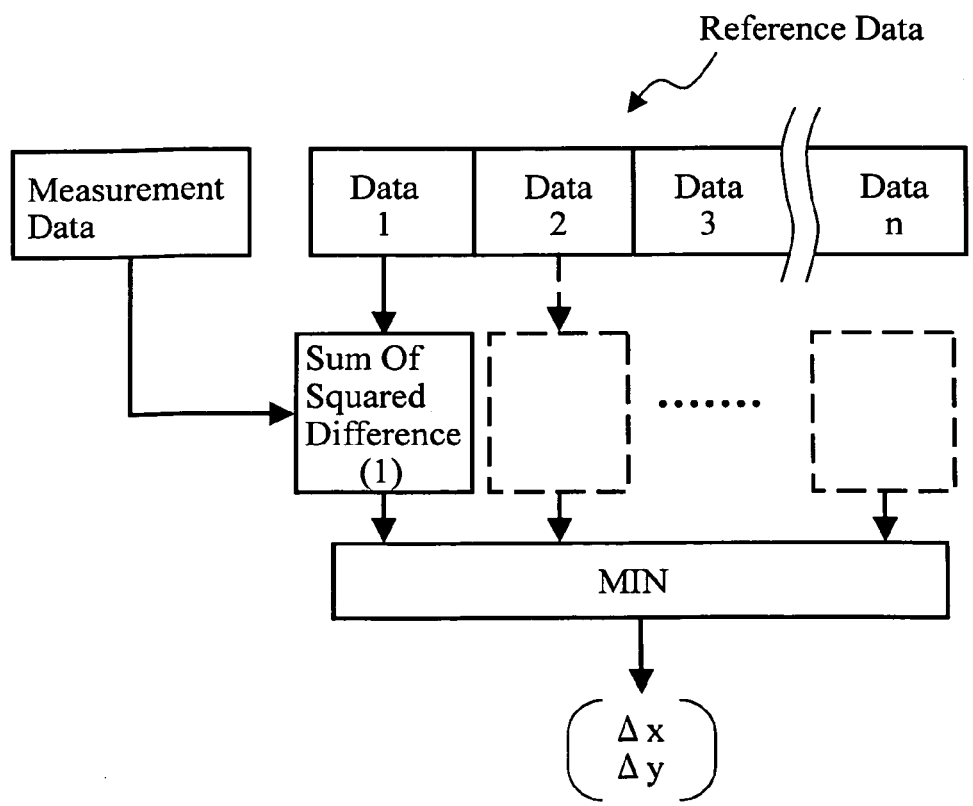
FIG. 5 is a diagram for explaining an SSD calculation method.

FIG. 5 is a diagram for explaining an SSD calculation method.

First, the pixel unit SSD calculating circuit 310 reads reference data of an image area of predetermined size (frame) serving as the unit of comparing process from the reference data memory 302 on the basis of positional information from the position circuit 107. At this moment, the pixel unit SSD calculating circuit 310 generates images shifted in parallel in units of pixels (displaced images) with respect to the reference data of such a frame. In FIG. 5, the generated images are shown as data 1, data 2, ... data n. The measurement data and the reference data in the frame are compared. For example, it is preferable to make an area of 512×512 pixels as one frame. Between each item of plural reference data displaced in units of pixels and the measurement data of the areas of the same size read from the measurement data memory 304, the SSD is calculated. The SSD is obtained by summing the squared residual between each pixel value of the reference data and each pixel value of the measurement data. Then, the SSD of each of the plural reference data is calculated, and the minimum value of the SSD is calculated. The measurement data and the reference data are aligned to a position where the minimum value is obtained. In this manner, it is possible to make alignment to the position where the measurement data and the reference data are positioned closest when shifted in parallel in x and y directions in units of pixels. Such a position is made as a preliminary alignment position, and a detailed alignment is performed hereinafter.

In step S206, as the sub-pixel image unit SSD calculating step, the sub pixel unit SSD calculating circuit 320 serving as one example of an SSD calculating unit performs displacement in units of pixels from the preliminary alignment position of the measurement data and the reference data, and calculates the displacement amount to the position where the SSD between the pixel value of the measurement data and the pixel value of the reference data is minimized.

The sub pixel unit SSD calculating method is the same as the contents explained in FIG. 5. On the basis of the preliminary alignment position, images shifted in parallel in units of pixels (displaced images) are generated with respect to the reference data of the size of the areas to be compared. In FIG. 5, the generated images are shown as data 1, data 2, ... data n. For example, as sub pixels, ⅛, 1/16, 1/32 and the like of one pixel are made into units. For example, when ⅛ of one pixel is made as the unit of the sub pixel, the reference data of areas of a predetermined size displaced by ±⅛ pixel, ±2/8 pixel, ±⅜ pixel, ±4/8 pixel, ±5/8 pixel, ±6/8 pixel, and ±7/8 pixel in the x direction and the y direction, respectively, and the reference data with the displacement amount of 0 are generated. That is, 256 kinds of reference data in a combination of 16 ways in the x direction, and 16 ways in the y direction are generated. Then, the SSD is calculated between the respective reference data and the respective measurement data. The SSD is obtained by summing the squared residual between each pixel value of the reference data and each pixel value of the measurement data. Then, the SSD of each of the plural reference data is calculated, and the minimum value of the SSD is calculated. In this manner, it is possible to obtain the displacement amount to the position where the minimum value is obtained. The data such as the set displacement amount and the calculated SSD are stored in the calculation data memory 330. In this manner, it is possible to obtain the displacement amount $(x_0, y_0)$ for alignment of the measurement data and the reference data to the position where they are positioned closest when shifted in parallel in the x and y directions in units of sub pixels.

In step S208, as the least-square method displacement calculating step, the least-square method displacement calculating circuit 322 serving as one example of a least-square method calculating unit calculates the displacement amount based on the least-square method from the above-mentioned preliminary alignment position of the measurement data and the reference data. Herein, by use of the least-square method as a statistical method, the displacement amount necessary for the alignment is calculated.

FIG. 6 shows a model equation for displacement amount calculation based on the least-square method.

As shown in FIG. 6, with respect to the reference data $U(x, y)$ serving as a reference image, the displacement amount $(x_0, y_0)$ of the measurement data $S(x, y)$ serving as an optical image (actual image) in the x and y directions and the image transmission loss ratio $\epsilon$ are supposed. In this case, $S(x, y)=(1-\epsilon)U(x-x_0, y-y_0)$ can be expressed as shown in the equation (1). By linearization on supposition that the transmission loss ratio is small enough, $\epsilon \cdot U + x_0 \cdot (dU/dx) + y_0 \cdot (dU/dy) = U - S$ is obtained as shown in the equation (2), wherein $dU/dx$ is a partial differential of U by x, and $dU/dy$ is a partial differential of U by y. Then, with respect to each pixel of an two-dimensional image, a value $(U-S)$ to be obtained by subtracting the measurement data serving as an actual image from the reference data, a value $(dU/dx)$ to be obtained by space differentiating the reference data in the x direction, and a value $(dU/dy)$ to be obtained by space differentiating the reference data in the y direction are obtained, and thereby a correlation matrix described below is obtained.

FIG. 7 shows a correlation matrix equation based on the least-square method.

The displacement amount $(x_0, y_0)$ and the transmission error ratio $\epsilon$ can be estimated by the least-square method by solving the correlation matrix equation shown in FIG. 7. Thereby, it is possible to obtain the displacement amount $(x_0, y_0)$ for alignment to the position where the reference data and the measurement data are positioned closest in the base based on the least-square method.

In step S210, as the SSD calculating step, the SSD calculating circuit 324 serving as one example of an SSD calculating unit calculates the SSD of the pixel value of the measurement data and the pixel value of the reference data at the position $(x-x_0, y-y_0)$ displaced by the displacement amount $(x_0, y_0)$ calculated by the least-square method displacement calculating circuit 322 from the above-mentioned preliminary alignment position of the measurement data and the reference data.

In step S212, as the determining step, the determining circuit 340 serving as one example of a determining unit determines which of the minimum SSD obtained as the result of the calculation by the sub pixel unit SSD calculating circuit 320 and the SSD obtained as the result of the calculation by the SSD calculating circuit 324 is smaller.

In step S214, as the position correcting step, the position correcting circuit 350 serving as one example of a position correcting unit corrects the alignment position of the measurement data and the reference data to a position where the smaller SSD determined by the determining circuit 340 is obtained. Further, it is preferable that the position correcting circuit 350 corrects the image gray level of each pixel of the reference data by use of the image strength fluctuation rate $\epsilon$ calculated by the least-square method displacement calculating circuit 322. For example, not only when the determining circuit 340 adopts the result calculated by the SSD calculating circuit 324, but also when the determining circuit 340 adopts the result calculated by the sub pixel unit SSD calculating circuit 320, the image strength of each pixel of the reference data is preferably corrected by use of the image strength fluctuation rate $\epsilon$ calculated by the least-square method displacement calculating circuit 322.

Herein, the SSD method and the least-square method have kinds of patterns for which they are better suited, respectively. For example, the SSD method is suited for aligning patterns of sparse figure density. On the other hand, the least-square method is suited for aligning patterns of dense figure density. For this reason, with the configuration as explained in the present embodiment, the SSD of the least-square method is compared with the minimum SSD of the SSD in units of sub pixels, and the correcting method with the smaller SSD among the SSD of the least-square method and the SSD in units of sub pixels is adopted, so that better results are expected than those in a case of correction made singly by each of the methods.

More specifically, in the case of an image of a sparse pattern, the calculation by the least-square method may become unstable, and thus, alignment by the SSD is adopted in that case. A parallel use of the SSD method and the least-square method makes it possible to stably correct even such a sparse pattern.

By correcting the reference data serving as a reference image or the measurement data serving as an optical image (actual image) by use of such a value, it is possible to make the measurement data and the reference data further closer to each other. As a result, it is possible to prevent a false detection in defect inspection, and to increase the practical sensitivity. As mentioned above, by simply correcting the displacement between the reference image and the actual image and the image strength fluctuation, a highly sensitive inspection can be realized.

Herein, the object to be compared in the determining step is not limited to the SSD, but the sum of the p-th power of a residual wherein p is a positive number may be adopted generally. The SSD corresponds to the case of P=2. In other words, a position correction by the SSD is performed in parallel with the least-square method, and the sum of the p-th power (p is a positive number) of the residual absolute value of the actual image and the corrected reference image is calculated in the respective cases of the correction by the least-square method and the correction by the SSD method, both of the values are compared with each other, and a correction method in which the sum of the p-th power of the residual absolute value becomes minimum may be selected.

In step S216, as the comparing step, the comparing circuit 108 aligns, by means of the alignment circuit 140, the optical image serving as a pattern image to be inspected generated by the sensor circuit 106 on the basis of the transfer image obtained from the photo mask 101 serving as a sample, and the reference image serving as an inspection standard pattern image generated by the developing circuit 111 and the reference circuit 112, and then takes in both the images. In addition, the comparing circuit 108 compares them with each other according to a predetermined algorithm, and determines whether there is a defect or not. By performing a data comparison through such a highly precise alignment, it is possible to prevent a false detection of a defect and to decrease nuisance defects, thereby performing a highly precise inspection.

Second Embodiment

In a second embodiment, a simple method for aligning measurement data and reference data of a one-dimensional pattern will be explained. Herein, since an apparatus configuration and the steps of a sample inspection method or an image alignment method in the second embodiment are same as those in the first embodiment, explanations thereof are omitted.

Figure 8:
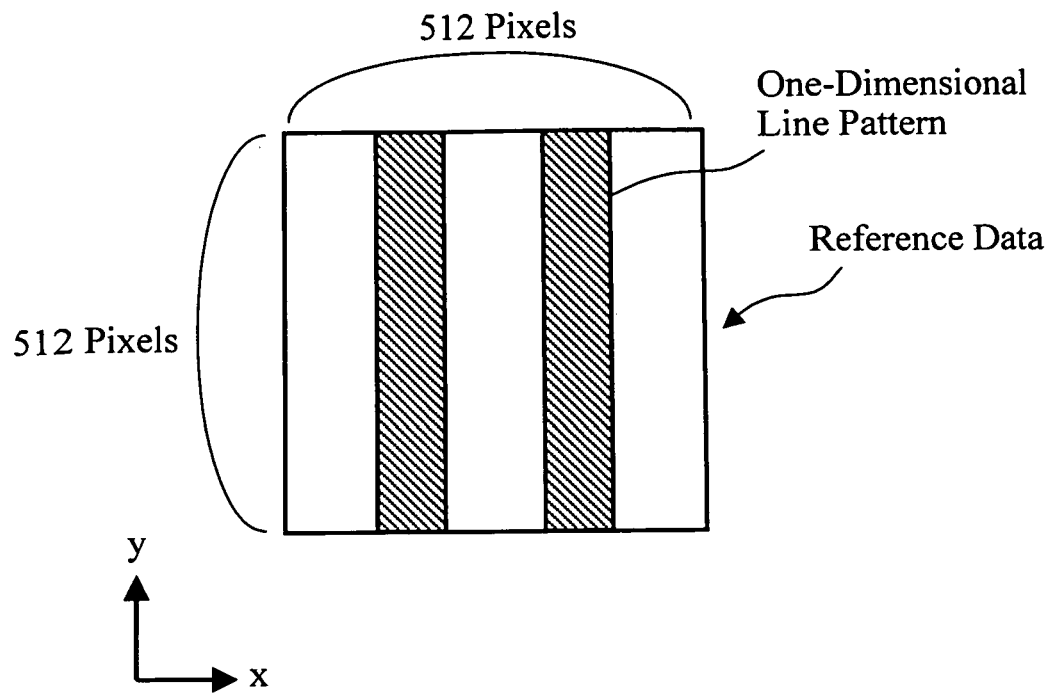
FIG. 8 is a diagram showing one example of a one-dimensional pattern (lines and spaces)

FIG. 8 is a diagram showing one example of a one-dimensional pattern.

Figure 9:
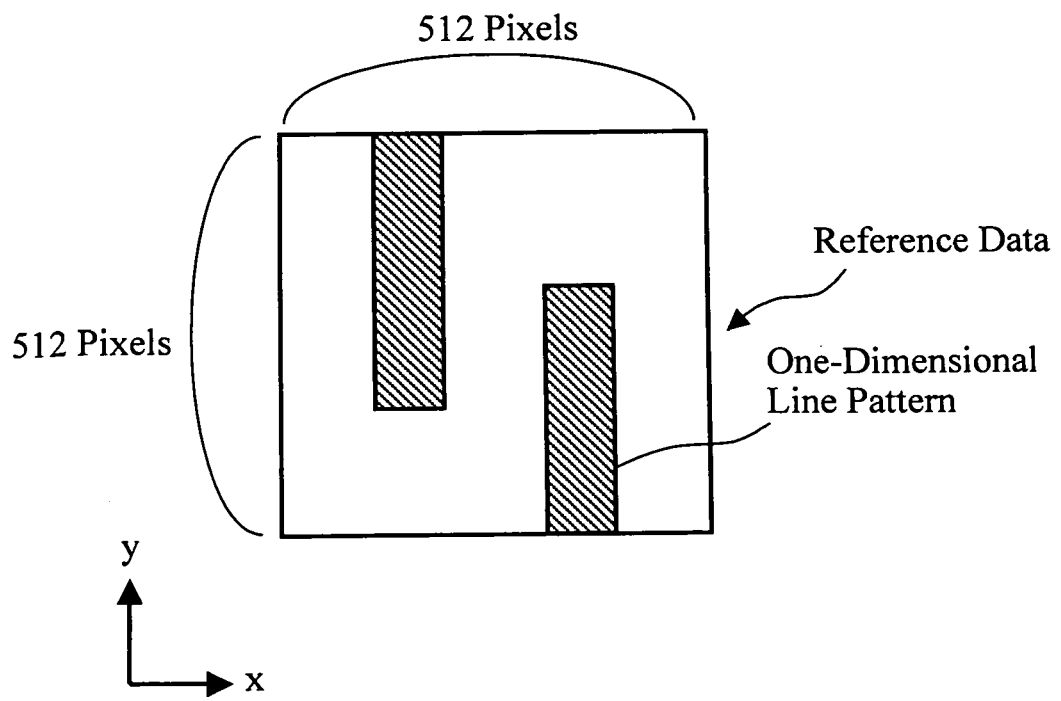
FIG. 9 is a diagram showing another example of a quasi-one-dimensional pattern.

FIG. 9 is a diagram showing another example of a one-dimensional pattern.

A model by the least-square method is suited for a two-dimensional pattern. However, in the case of a one-dimensional pattern such as a line/space, a regular matrix may be out of the rank, and one of $x_0$ and $y_0$ may become unstable. In the examples in FIGS. 8 and 9, $y_0$ becomes unstable.

FIG. 10 shows a correlation matrix equation in the case where $y_0$ becomes unstable.

For example, when $\Sigma(dU/dx)^2$ and $\Sigma(dU/dy)^2$ as diagonal sections of the regular matrix are compared with each other in the case where $y_0$ becomes unstable, $\Sigma(dU/dy)^2$ is negligible in comparison with $\Sigma(dU/dx)^2$ as shown in the equation 10. Therefore, as shown in the equation 12, by deleting the term including (dU/dy) from the correlational sum of the regular matrix, the regular matrix can be degenerated from 3×3 to 2×2. This derived matrix is solved to obtain $\epsilon$ and $x_0$, so that it is possible to perform position correction and image resolution correction.

FIG. 11 is a diagram showing still another example of a one-dimensional pattern.

Figure 12:
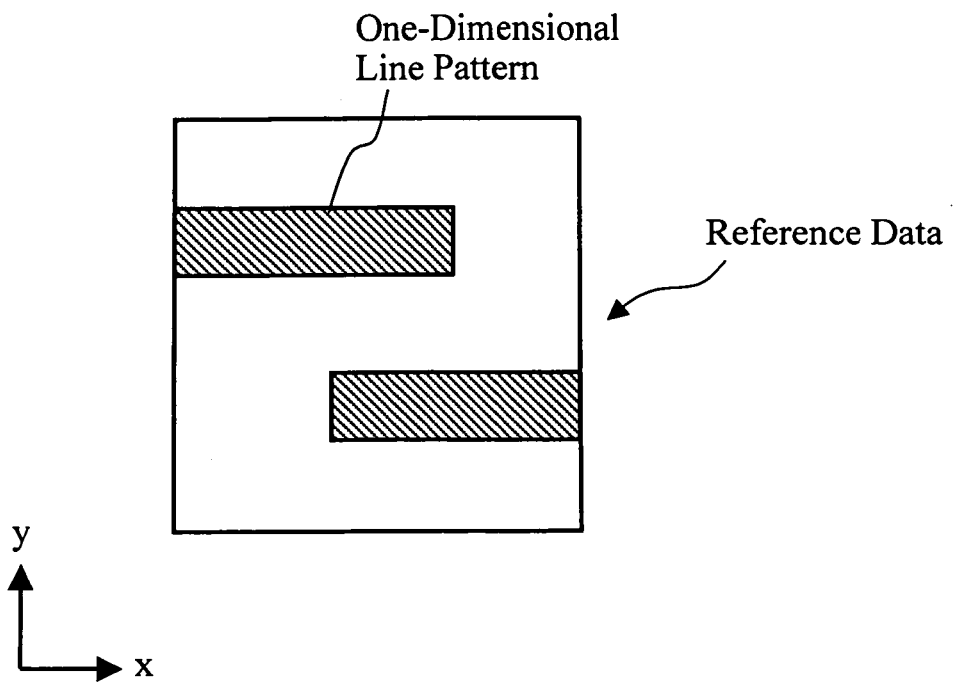
FIG. 12 is a diagram showing further another example of a one-dimensional pattern (lines and spaces)

FIG. 12 is a diagram showing further another example of a one-dimensional pattern.

On the contrary to the above-mentioned case, $x_0$ becomes unstable in the examples in FIGS. 11 and 12.

In such a case, when $\Sigma(dU/dx)^2$ and $\Sigma(dU/dy)^2$ as diagonal sections of the regular matrix are compared with each other, $\Sigma(dU/dx)^2$ is negligible in comparison with $\Sigma(dU/dy)^2$. Therefore, on the contrary to the above case, by deleting the section including (dU/dx), the regular matrix can be degenerated from 3×3 to 2×2. This derived matrix is solved to obtain $\epsilon$ and $y_0$, whereby it is possible to perform position correction and image resolution correction.

As described above, when one of the value obtained by space differentiating the reference image in the x direction and the value obtained by space differentiating the reference image in the y direction is smaller than specified times of the other, the least-square method displacement calculating circuit 322 deletes the smaller for calculation. As a result, in a model by the least-square method, it is possible perform an estimation by automatically reducing the number of estimation parameters even in the case of instability in a basic model like a line system.

Herein, even when, for example $x_0$ turns unstable in performing only the position correction of a line system, with regard to the x direction, it is preferable to adopt the shift amount in the x direction of the SSD in units of sub pixels used in parallel in order to perform the position correction. In practice, even if it is difficult to distinguish a one-dimensional pattern and a two-dimensional pattern, a more stable alignment result can be obtained than the case where the unstable $x_0$ is fixed to, for example, "0". In the same manner, even if, for example, $y_0$ becomes unstable, with regard to the y direction, it is preferable to adopt the shift amount in the y direction of the SSD in units of sub pixels used in parallel in order to perform the position correction. Further, when one of the value obtained by space differentiating the reference image in the x direction and the value obtained by space differentiating the reference image in the y direction is smaller than specified times of the other, the SSD calculating circuit 324 preferably calculates by substituting the displacement amount obtained by the sub pixel unit SSD calculating circuit 320 as the displacement amount in the smaller direction of the x direction and the y direction.

Third Embodiment

In a third embodiment, a method for correcting a local displacement in a frame will be explained. Herein, since an apparatus configuration and the steps of a sample inspection method or an image alignment method in the third embodiment are same as those in the first embodiment, explanations thereof are omitted.

Figure 13:
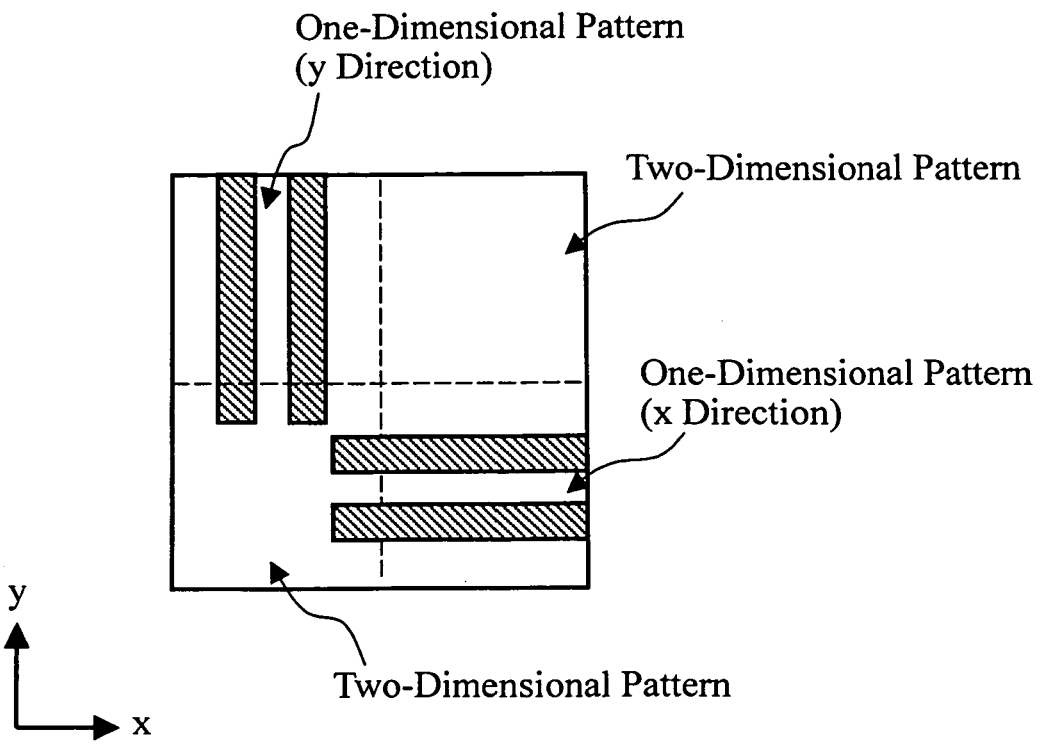
FIG. 13 is a diagram showing one example of a two-dimensional pattern.

FIG. 13 is a diagram showing one example of a two-dimensional pattern.

For example, in the case where a local displacement occurs in a part of the two-dimensional pattern shown in FIG. 13, it is difficult to move the entire frame in the x and y directions in the SSD. In the least-square method, on the other hand, it is preferable to divide such a frame by, for example, dot lines as shown in FIG. 13; calculate the displacement amount in each of the divided areas; and estimate the displacement amount and the image transmission loss ratio, respectively. In such a case, when the divided areas are configured by a one-dimensional pattern, the regular matrixes can be degenerated from 3×3 to 2×2, respectively, when either $x_0$ or $y_0$ becomes unstable, as explained in the second embodiment. Consequently, it is possible to perform a highly precise displacement correction by composing the respective divided areas.

Further, in the last-square method, when the above-mentioned frame is divided by, for example, dot lines as shown in FIG. 13, it is preferable to divide the frame by weighting; calculate the displacement amount in each of the divided areas; and estimate the displacement amount and the image strength fluctuation rate, respectively.

Figures 14, 15:
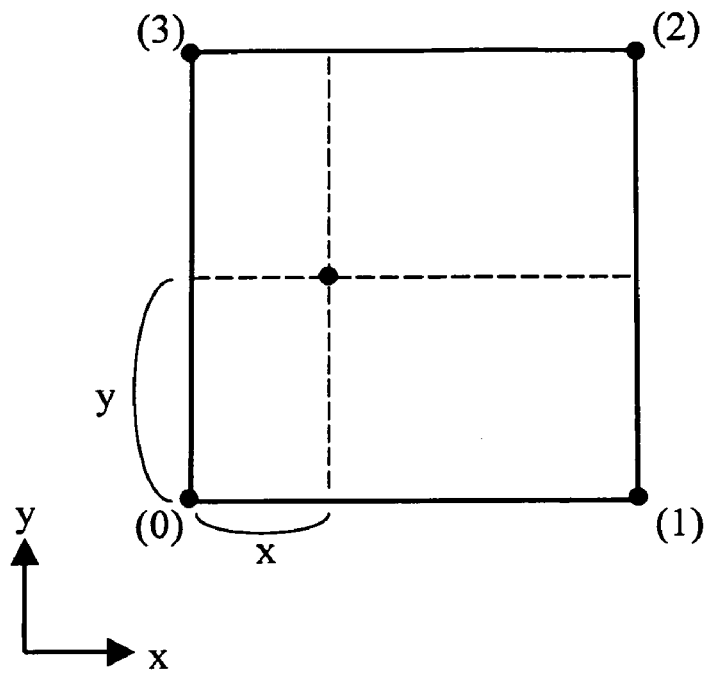
FIG. 14 is a diagram for explaining weighting with two-dimensional linear interpolation.
FIG. 15 shows an equation for weighting at neiboring four points.

FIG. 14 is a diagram for explaining weighting by one-dimensional linear interpolation.

FIG. 15 shows an equation for weighting at neiboring four points.

For example, with regard to certain image data P, when a pixel P is interpolated by use of image data of four points (0, 1, 2, 3) therearound, the reference data $U_{(0)}$ can be expressed by $U_{(0)}=(1-x)\cdot(1-y)\cdot U$, the reference data $U_{(1)}$ can be expressed by $U_{(1)}=x\cdot(1-y)\cdot U$, the reference data $U_{(2)}$ can be expressed by $U_{(2)}=x\cdot y\cdot U$, and the reference data $U_{(3)}$ can be expressed by $U_{(3)}=(1-x)\cdot y\cdot U$. The correlation matrix is calculated by use of the weighted reference data $U_{(0)}$, reference data $U_{(1)}$, reference data $U_{(2)}$, and reference data $U_{(3)}$.

FIG. 16 shows a correlation matrix equation in the third embodiment.

When weighting is performed at neiboring four points, the correlation matrix equation shown in FIG. 16 is solved to obtain 12 variables including image transmission loss ratio $\epsilon_{(0)}$, $\epsilon_{(1)}$, $\epsilon_{(2)}$ and $\epsilon_{(3)}$, and the displacement amounts $x_{0(0)}$, $x_{0(1)}$, $x_{0(2)}$, $x_{0(3)}$, $y_{0(0)}$, $y_{0(1)}$, $y_{0(2)}$, and $y_{0(3)}$. Position correction is performed by use of such values to correct a local displacement and the like in the frame. The causes of the local displacement include (1) snaking of an XY stage, (2) a difference in image size between an actual image and a reference image, and (3) a difference in image size between image scanning elements. The weighting method is not limited to the one using neiboring four points, but it is preferable to adopt bicubic interpolation using 16 points, or the like. In FIG. 16, description of values of the matrix is partly omitted.

Figure 17:
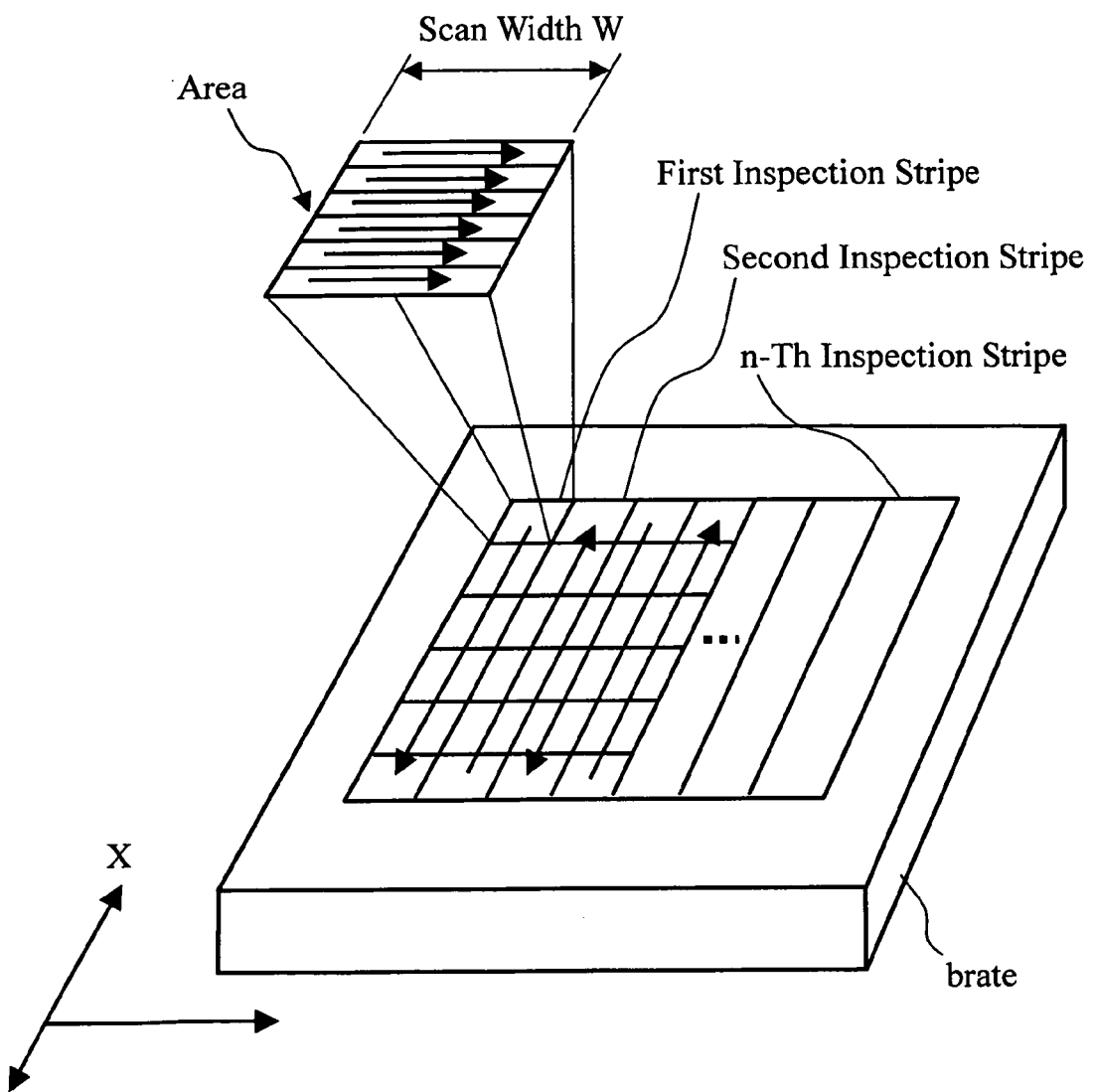
FIG. 17 is a diagram for explaining another method for obtaining an optical image.

FIG. 17 is a diagram for explaining another method for obtaining an optical image.

In the configuration in FIG. 1, the photodiode array 105 which simultaneously emits beams corresponding the number of pixels (for example, 2048 pixels) of the scan swath W is employed, but the present invention is not limited thereto. As shown in FIG. 17, an alternative method may be used in which, while the XYθ table 102 is transferred at a constant speed in the X direction, a laser scanning optical device (not shown) scans with a laser beam in the Y direction at every time when movement of a predetermined pitch is detected by a laser interferometer, and transmitted light is detected to acquire a two-dimensional image in every area having a predetermined size.

In the above explanation, the various circuits and the various steps described above can be constituted by programs which can be operated by a computer. Alternatively, the circuits and the steps may be realized not only by programs serving as software but also by a combination of hardware and software. Alternatively, a combination of software and firmware may be used. When the circuits and the steps are constituted by programs, the programs are recorded on a recording medium such as a magnetic disk device, a magnetic tape device, an FD, or a read only memory (ROM). For example, the table control circuit 114, the developing circuit 111, the reference circuit 112, the comparing circuit 108, the alignment circuit 140, the respective circuits in the alignment circuit 140, and the like may be constituted by electric circuits or the like, or may also be realized as software processed by the control computer 110. These circuit may also be realized by combinations of electric circuits and software.

As described above, according to at least one of the above-mentioned embodiments, it is possible to correct the alignment position of an optical image and a reference image by the optimum displacement amount from among the displacement amount to become the minimum SSD obtained as the result of SSD calculation and the displacement amount obtained as the result of least-square method calculation. More specifically, the alignment position can be corrected by a more preferable optimizing method depending on an image. Thereby, a further highly precise alignment becomes possible. As a consequence, a highly sensitive inspection can be performed.

The embodiments have been described with reference to the concrete examples. However, the present invention is not limited to these concrete examples. For example, in the embodiments, transmitted light is used, but reflected light may be used, or transmitted light and reflected light may be used simultaneously. The reference image is generated from design data, but alternatively, data of a same pattern picked up by a sensor such as a photodiode array or the like may be employed. In other words, it is equally preferable to employ the die to die inspection or the die to database inspection.

In the apparatus configurations, the control methods, and the like, parts or the like which are not directly required to explain the present invention are not described. However, a necessary apparatus configuration and a necessary control method can be appropriately selected and used.

All sample inspection apparatuses and all sample inspection methods which have the constituent elements of the present invention and which can be appropriately changed in design by a person skilled in the art are included in the spirit and scope of the invention.

Additional advantages and modification will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A sample inspection apparatus comprising:
an optical image scanning unit configured to scan an optical image of a sample to be inspected;
a reference image generating unit configured to generate a reference image to be compared with the optical image on the basis of design data of the sample to be inspected;
a first SSD (Sum of the Squared Difference) calculating unit configured to calculate the displacement amount from a preliminary alignment position of the optical image and the reference image to a position where the SSD (Sum of the Squared Difference) of a pixel value of the optical image and a pixel value of the reference image becomes minimum;
a least-square method calculating unit configured to calculate the displacement amount from the preliminary alignment position of the optical image and the reference image, by least-square method by solving a correlation matrix equation using a value obtained by space differentiating the reference data in the x direction and a value obtained by space differentiating the reference data in the y direction;
a second SSD calculating unit configured to calculate the SSD of the pixel value of the optical image and the pixel value of the reference image at a position displaced by the displacement amount calculated by the least-square method calculating unit from the preliminary alignment position of the optical image and the reference image;
a determining unit configured to determine which of a minimum SSD obtained as the result of the calculation by the first SSD calculating unit and the SSD obtained as the result of the calculation by the second SSD calculating unit is a smaller SSD;
a position correcting unit configured to correct the preliminary alignment position of the optical image and the reference image to a position where the smaller SSD determined by the determining unit is obtained; and
a comparing unit configured to compare the optical image and the reference image whose alignment position has been corrected.

2. The sample inspection apparatus according to claim 1, wherein the first SSD calculating unit calculates the displacement amount to the position where the SSD becomes minimum while displacing in units of sub pixels.

3. The sample inspection apparatus according to claim 1, wherein the least-square method calculating unit: when one of the value obtained by space differentiating the reference image in the x direction and the value obtained by space differentiating the reference image in the y direction is smaller than specified times of the other, performs calculation by deleting the smaller value.

4. The sample inspection apparatus according to claim 1, wherein the least-square method calculating unit divides the reference image, and calculates the displacement amount in each of the divided areas.

5. The sample inspection apparatus according to claim 1, wherein the least-square method calculating unit divides the reference image by weighting, and calculates the displacement amount in each of the divided areas.

6. The sample inspection apparatus according to claim 1, wherein the least-square method calculating unit calculates an image strength fluctuation rate as well as the displacement amount, and the position correcting unit corrects the pixel value of the reference image on the basis of the image strength fluctuation rate.

7. The sample inspection apparatus according to claim 3, wherein, when one of the value obtained by space differentiating the reference image in the x direction and the value obtained by space differentiating the reference image in the y direction is smaller than specified times of the other, the displacement amount obtained by the first SSD calculating unit is substituted as the displacement amount in the smaller direction of the x direction and the y direction.

8. The sample inspection apparatus according to claim 6, wherein, when the determining unit determines that the first SSD is smaller, the image strength fluctuation rate is corrected.

9. A computer readable recording medium having recorded therein program instructions which when executed by a computer results in performance of steps comprising:
storing an optical image and a reference image used for a comparison inspection of a sample to be inspected in a storage device;
a first SSD calculating step of calculating the displacement amount from a preliminary alignment position of the optical image and the reference image to a position where a SSD (Sum of the Squared Difference) between a pixel value of the optical image and a pixel value of the reference image becomes minimum by reading the optical image and the reference image from the storage device;
reading the optical image and the reference image from the storage device and calculating the displacement amount from the preliminary alignment position of the optical image and the reference image, by a least-square method by solving a correlation matrix equation using a value obtained by space differentiating the reference data in the x direction and a value obtained by space differentiating the reference data in the y direction;
a second SSD calculating step of calculating the SSD of the pixel value of the optical image and the pixel value of the reference image at a position displaced by the displacement amount calculated by the least-square method calculating process from the preliminary alignment position of the optical image and the reference image;
determining which of a minimum SSD obtained as the result of the calculation by the first SSD calculating step and the SSD obtained as the result of the calculation by the second SSD calculating step is a smaller SSD; and
correcting the alignment position of the optical image and the reference image to a position where the smaller SSD determined by the determining is obtained; and
comparing the optical image and the reference image whose alignment position has been corrected.

* * * * *